United States Patent [19]

Schwarz et al.

[11] Patent Number: 5,616,784

[45] Date of Patent: Apr. 1, 1997

[54] THERMAL CLEAVAGE OF CARBAMIC ESTERS

[75] Inventors: Hans V. Schwarz, Waterloo, Belgium; Andreas Otterbach, Frankenthal, Germany; Otto Mattner, Speyer, Germany; Franz Merger, Frankenthal, Germany; Wolfgang Schwarz, Otterstadt, Germany; Eckhardt Brandt, Schifferstadt, Germany; Peter Magnussen, Bad Duerkheim, Germany; Roland Minges, Gruenstadt, Germany

[73] Assignee: BASF Aktiengesellschaft, Ludwigshafen, Germany

[21] Appl. No.: 570,250

[22] Filed: Dec. 11, 1995

Related U.S. Application Data

[63] Continuation of Ser. No. 105,661, Aug. 13, 1993, abandoned, which is a continuation of Ser. No. 915,640, Jul. 21, 1992, abandoned.

[30] Foreign Application Priority Data

Jul. 25, 1991 [DE] Germany .......................... 41 24 671.3

[51] Int. Cl.⁶ .................................................. C07C 45/00
[52] U.S. Cl. .............................................................. 560/345
[58] Field of Search ............................................... 560/345

[56] References Cited

U.S. PATENT DOCUMENTS

| | | | |
|---|---|---|---|
| 2,822,373 | 2/1958 | Beck | 560/347 |
| 2,823,221 | 2/1958 | Pfirschke et al. | 560/347 X |
| 3,734,941 | 5/1973 | Sydor | 560/345 |
| 3,896,006 | 7/1975 | Cooke | 203/28 |
| 4,081,472 | 3/1978 | Tsumura et al. | 560/345 |
| 4,162,263 | 7/1979 | Zanker | 260/453 |
| 4,289,732 | 9/1981 | Bauer et al. | 422/224 |
| 4,294,774 | 10/1981 | Henson et al. | 560/345 |
| 4,386,033 | 5/1983 | König et al. | 260/453 |
| 4,692,550 | 9/1987 | Engbert et al. | 560/345 |
| 5,087,739 | 2/1992 | Bohmholdt | 560/345 |

*Primary Examiner*—Samuel Barts
*Attorney, Agent, or Firm*—Keil & Weinkauf

[57] ABSTRACT

In a reactor for the thermal cleavage of mono- and polyfunctional carbamic esters into the corresponding isocyanates and the hydroxyl component in the liquid phase, the geometry of the reactor, defined by the degassing area in relation to the volume and the arrangement of the heating surfaces, permits cleavage in a two-phase mixture which has a volumetric gas content of more than 50%.

9 Claims, No Drawings

THERMAL CLEAVAGE OF CARBAMIC ESTERS

This application is a continuation of application Ser. No. 08/105,661, filed on Aug. 13, 1993, now abandoned, which is a continuation of application Ser. No. 07/915,640, filed on Jul. 21, 1992 now abandoned.

The present invention relates to a process for the thermal cleavage of mono- and polyfunctional carbamic esters into the corresponding isocyanates and the hydroxyl component in the liquid phase and for isolating the resulting isocyanate, in which the novel reactor is integrated.

Reactors for the cleavage of carbamic esters into isocyanates have been described in various patents. The cleavage of the carbamic esters after vaporization in the gas phase is described in, for example, European Patents 28,724, 126, 299, 126,300 and 100,047 and in U.S. Pat. Nos. 3,734,941 and 3,870,739. The disadvantage here is the danger of blockage in the upstream evaporator, which makes industrial use more difficult.

The cleavage in a fluidized bed or a stirred bed of carbon powder after atomization of the carbamic ester into this bed, described in European Patent 78,005, gives good yields but is likely to give rise to difficulties in industrial implementation.

Cleavage in the liquid phase makes it necessary to remove at least one of the two cleavage products, i.e. the isocyanate or the hydroxyl component, in gaseous form immediately from the reaction solution in order to prevent a reverse reaction. Advantageously, both cleavage products are removed in gaseous form and subsequently separated. Owing to the formation of relatively high molecular weight irreversible byproducts it is necessary continuously to remove some of the reaction medium in the reactor and thus to separate off the byproducts.

In order to suppress side reactions which give irreversible decomposition products, it is useful to reduce the reaction temperature with the aid of catalysts. However, basic catalysts, described in U.S. Pat. Nos. 2,692,275 and 2,713,591, accelerate the decomposition reactions too. More suitable catalysts for the cleavage of aromatic carbamic esters are described in DES 2,625,490. Aluminum, zinc and tin compounds dominate. They are used in concentrations of substantially less than 1% and preferentially accelerate the cleavage reaction.

For the preparation of polyfunctional isocyanates where there is a greater danger of polymerization and residue formation, the dilution of the carbamic esters with inert solvents, described in German Published Applications DAS 2,421,503 and DAS 2,526,193, or the metering of inert solvents into the cleavage reactor, described in European Patent 92,738, was proposed in order to suppress coating of the surfaces in the reactor and to separate off byproducts. The disadvantages of such an addition of assistants are the resulting more complicated process engineering and the costs of its use.

U.S. Pat. No. 4,294,774 proposes cleavage in catalytic solvents, such as dialkylanilines.

In European Patent 92,738, however, solvent-free cleavage is not ruled out. Thin film evaporators and falling film evaporators are mentioned as suitable reactors. The disadvantages of these reactors are moving parts in the preferred thin film evaporator, the high costs of such reactors on an industrial scale and, as the most important disadvantage, the susceptibility of such reactors to blockage as a result of polymerization in the cleavage of polyfunctional carbamic esters if the reactors are operated continuously over a period longer than a few days, which is unavoidable for a cost-efficient industrial reactor. The reactors described thus all have deficiencies with regard to their suitability for industrial use.

It is an object of the present invention to provide a process in which the catalyzed or uncatalyzed cleavage of carbamic esters can be carried out continuously over industrially useful periods without the use of a solvent or diluent and without operation having to be interrupted owing to blockage or fouling by polymeric byproducts.

It was also necessary to find a method for removing the cleavage gases from the reactor and for separating them, which method is likewise free of blockage and fouling problems. In addition, the presence of byproducts, as may occur in a circulation method for the production of isocyanates from amines via the intermediate of the carbamic esters, in the reactor must be possible without the stated problems once again occurring as a result.

We have found that this object is achieved, according to the invention, if the geometry of the reactor, defined by the degassing area in relation to the volume and the arrangement of the heating surfaces, permits cleavage in a two-phase mixture which has a volumetric gas content of more than 50%.

We have found, surprisingly, that carbamic esters, in particular bifunctional and polyfunctional carbamic esters, can be cleaved, with long service lives of the reactors and good yields, not only in technically demanding apparatuses, such as falling film evaporators, thin film evaporators and stirred reactors, but also in simple reactors described in detail below and having no moving parts, without it being necessary to use solvents or diluents. It was surprising in particular that service lives of several months of continuous operation could be achieved without the reactor having to be shut down owing to coating with polymeric byproducts.

Suitable reactors are kettles which contain baffles for introducing the heat of reaction. The reaction medium is present therein in a state resembling boiling, wherein the educt vapors and gases resulting from the cleavage reaction are formed and rise in the liquid.

The resistance to polymeric coating is achieved by the special geometry of the reactors and the operation of the reactors in an operating state not conventionally used industrially to date: the reactor is operated in such a way that the two-phase mixture of boiling liquid and vapor phase, which consists of the vaporized educt and the cleavage gases, has a volumetric gas content of more than 50%. The reaction is accordingly carried out in a flow state not conventionally used in industrial evaporators to date. More than 70% of the liquid or less than 30% gas content in the vaporizing medium are customary in the heated evaporator zone. Gas contents greater than 30% (apparent liquid state of less than 70%) leads, in conventional industrial evaporators, to poorer heat transfer and other disadvantages, for example breakdown of the natural circulation in Robert evaporators. Relationships between evaporator characteristics and the volumetric gas content of the medium are described, for example, in Strömung und Wärmeübergang in Gas-Flüssigkeits-Gemischen, Franz Mayinger, Springer Verlag, 1982, Sections 1.3 and 2.4, and in the habilitation dissertation entitled Partielles Filmsieden in Zweiphasenströmungen by Dr. Ing. habil. Hein Auracher, Progress Reports VDI, Series 3 Verfahrenstechnik, No. 142, VDI-Verlag 1987, and in Evaporation Technology by Reinhard Billet, Verlag Chemie, Weinheim, 1989, pages 114–119. This mode of operation thus goes beyond the conventional prior art.

The volumetric gas content of the two-phase mixture should be from 50 to 98%, preferably from 60 to 96%, particularly preferably from 75 to 90%.

To realize such high gas contents in the two-phase mixture, certain geometric requirements for the reactors are useful.

For example, it is useful to choose the height of the reaction zone in the reactor to be no less than 0.2 m and no greater than 2 m, in order to promote the formation of gas-rich two-phase mixture. The degassing area of the reactor should be such that the gas velocity is not less than 1 m/s and not more than 30 m/s. The heat transfer areas should have dimensions such that the temperature difference between the heating medium and the reaction medium is less than 40° C. but at the same time the quantity of heat required for the highly endothermic reaction can be introduced into the volume restricted by residence time requirements.

According to these requirements, suitable cleavage reactors are Robert evaporators, Herbert evaporators with and without forced circulation, heating cartridge evaporators having vertical, inclined or horizontal heating cartridges, Caddie-type evaporators, kettles having closely wound heating coils and similar reactors which are distinguished by a high level of heat introduction into a small volume. The reactors are operated completely continuously both with regard to product feed and with respect to removal of liquid, in order to avoid concentration of more highly boiling byproducts. The conversion in the reactor per pass is from 30 to 95%, preferably from 60 to 90% for the transformation of urethane in the reactor feed into isocyanate removed. The residence time of the boiling liquid in the reactor is several minutes and cannot be regarded as very short, constituting a substantial difference compared with the thin film reactors mentioned in European Patent 92,738.

The residence times are 1–60, preferably 5–30, minutes and are defined as the quotient of the liquid content of the reactor under reaction conditions and the reactor content removed in liquid form per minute from the reactor.

The reaction is carried out without any addition of solvent or diluent and without an inert gas being passed through the reactor. This is in contrast to European Patent 92,738, where diluents are expressly permitted.

It is essential for the invention that the stated reactors can be operated, while maintaining the boundary conditions described, in such a way that it is also possible to cleave polyfunctional carbamic esters into polyfunctional isocyanates and the particular hydroxyl component without the reactors having to be shutdown and cleaned in the course of a continuous operating time of several weeks. Thus, in contrast to reactors described above, the precondition for continuous industrial operation of such reactors is fulfilled.

Definition of the Reactor Feed

The reactor is charged with a product mixture which consists of the carbamic ester and of byproducts which are formed in a circulation process, wherein a carbamic ester is prepared from an amine with the aid of urea and a hydroxyl component and is then cleaved into the isocyanate, some of the reactor content being removed from the reactor and being recycled to the first stage of the process. Such byproducts may include substituted ureas, biurets, isocyanurates, allophanates, alkyl carbamates and dialkyl carbonates. Surprisingly, it is sufficient for the content of carbamic ester in the reactor feed to be from 80 to 90%. A higher purity of the carbamic ester facilitates operation of the cleavage reactor since in this case fouling problems become less important. It is also possible to use reactor feeds containing less than 80% of carbamic ester, but fouling problems then increase, particularly when polyfunctional carbamic esters are cleaved. The cleavage reactor feed may contain the catalyst used for cleavage.

One essential feature of the invention is the fact that the carbamic ester need not be completely vaporized and condensed again before being fed to the reactor, in order to free it from the oligomeric by-products, as described in European Patent 355 443-A2, but that a certain level of byproduct can be tolerated in the reactor.

Separation and Working-Up of the Gases Escaping From the Reactor:

The gases escaping from the reactor consist of the cleavage gases, ie. isocyanate and hydroxyl component, of vaporized starting material and of gaseous byproducts.

In contrast to European Patents 54,817, 92,738 and 355,443, cleavage gases are not subjected to fractional condensation in a plurality of successive dephlegmators but are rectified in a distillation column mounted directly on the cleavage reactor. Surprisingly, the complication described in European Patent 54,817, whereby the cleavage products recombine in the column when a rectified column is used instead of dephlegmators for removal of the cleavage gases and little or no cleavage product is obtained, did not occur. In contrast to the complication described, it was even possible to achieve a particularly good separation effect both with regard to the object of retaining unreacted carbamic ester in the reactor and with respect to the object of obtaining a hydroxyl component-rich and an isocyanate-rich product stream from the column.

The essential observation on which the present invention is based is therefore that it is possible to carry out the separation of the gases escaping from the reactor into the educt carbamic ester and into the products hydroxyl component and isocyanate in a rectifying column which is mounted directly on the reactor and has at least one reflux to the top of the column and either contains a take-off for a gaseous product stream at the top of the column, which stream is further worked up in downstream separating apparatuses, or contains a take-off of one of the two products as a side stream from the column and a take-off of the other product at the top of the column.

Further Processing of the Liquid Reacted Mixture

The liquid reacted mixture consists of unconverted carbamic ester and, in the case of the cleavage of polyfunctional carbamic esters, of partially converted starting material, and of components as already mentioned in the description of the reactor feed, but having a different percentage composition. As a rule, the reacted mixture consists of less than one third of unconverted educt. Before the reacted mixture is recycled to the first process stage, it may be reacted with the hydroxyl component from the cleavage reaction to saturate free isocyanate groups and freed from undesirable byproducts by distillation or another suitable separation operation.

EXAMPLE 3.6 kg/h of a mixture of 83% by weight of hexa-methylene-1,6-di-n-butylurethane, referred to below as HDU for short, about 15% by weight of oligomeric isocyanurates and smaller amounts of other byproducts, as stated in the general part, are fed, together with 0.01 mol %, based on HDU, of dibutyltin dilaurate, continuously into a heating cartridge reactor which contains 4 vapor-heated heating cartridges having a diameter of 14 mm and a length of 50 cm in a cylindrical space having a diameter of about 6.8 cm and a length of 52 cm. An outlet orifice of 12 mm diameter for liquid reactor content is located at the bottom of the reactor, between the heating cartridges. Above the reaction zone, the reactor widens to form a hood of 20 cm diameter and 30 cm height.

The cleavage reaction is carried out at 240° C. in the reaction medium and at a pressure of 30 mbar. The vapor temperature at the heating cartridges is about 260° C.

The volumetric gas content of the reaction mixture is about 84%, ie. the two-phase mixture filling the entire reaction space of about 1.6 l contains about 250 ml of liquid and about 1.35 l of gas or vapor.

About 1 kg/h of reactor discharge, which consists of 25% by weight of HDU, 9% by weight of isocyanatohexamethylene-n-butylurethane (HMI) and about 66% by weight of higher molecular weight allophanates, ureas, isocyanurates and further components difficult to define, is removed at the bottom of the reactor. In addition, the reactor discharge contains the total amount of tin from the reactor feed. The residence time of the reaction medium in the reactor is thus about 15 minutes.

The cleavage gases are separated in a rectifying column which is filled with Sulzer packing and is located directly on the stated hood above the reactor. HDU and HMI are separated off in the lower parts of the column and flow back into the reactor. A side take-off, from which about 1.2 kg/h of hexamethylene 1,6-diisocyanate (HDI) having a purity of about 98% by weight are removed, is located 80 cm above the reactor. A top condenser, from which about 1.4 kg/h of a butanol-rich top take-off is removed and a reflux is generated, is present 40 cm above the side take-off. The butanol-rich products removed at the top of the column are obtained with a purity of more than 99% by weight. The molar conversion of HDU in the reactor feed into HDI removed is thus about 76% in one reactor pass.

The reactor discharge and the butanol eliminated are conveyed to a stirred kettle and reacted there at 100° C. The resulting mixture is recycled to the urethane formation stage of a circulation process. In said stage, the carbamic ester HDU is prepared from hexamethylenediamine (HMD), urea and n-butanol and, after a plurality of purification steps, is then fed to the cleavage reactor in the form of the mixture containing byproducts.

The crude HDI obtained at the side take-off of the rectifying column is brought to commercial purity in suitable purification stages. The yield of HDI in the circulation process was 93% based on hexamethylenediamine and 89% based on urea.

After uninterrupted operation for 8 weeks, the cleavage reactor had only slight coatings on the heating surfaces and never had to be cleaned during this period.

We claim:

1. A process for removing cleavage products formed in the thermal cleavage of carbamic esters in a reactor consisting of:

passing the products directly from the reactor to a rectifying column, said column having a reflux to the top of the column and having one or more take-off points through which gaseous or liquid product or product mixture is removed.

2. A process as defined in claim 1, wherein the rectifying column contains a side take-off and a top take-off for liquid or gaseous isocyanate or hydroxyl component.

3. A process as defined in claim 1, wherein rectification is carried out at less than 500 mbar.

4. A process as defined in claim 1, wherein rectification is carried out at less than 100 mbar.

5. A process as defined in claim 1, wherein the column has a reflux at the top and the mixture of hydroxyl component and isocyanate component is taken off in gaseous form at the top of the column.

6. A process for the thermal cleavage of mono- and polyfunctional carbamic esters into the corresponding isocyanates and the hydroxyl component in a liquid phase of a reactor, which reactor contains a gas/liquid reaction mixture of which the gas content is greater than 50% by volume, wherein the residence time of the reaction mixture is from 1 to 60 minutes.

7. The process of claim 6, wherein the process is carried out in the absence of added solvent.

8. The process of claim 6, wherein the process involves the conversion of urethane into isocyanate and this conversion is not less than 50% in one pass.

9. The process of claim 6, wherein the pressure in the reactor is from 1–500 mbar.

* * * * *